United States Patent [19]
Berg

[11] Patent Number: 5,602,294
[45] Date of Patent: Feb. 11, 1997

[54] SEPARATION OF O-XYLENE FROM P-XYLENE AND M-XYLENE BY EXTRACTIVE DISTILLATION

[76] Inventor: Lloyd Berg, 1314 S. Third Ave., Bozeman, Mont. 59715

[21] Appl. No.: 455,855

[22] Filed: May 31, 1995

[51] Int. Cl.$^6$ .................... B01D 3/40; C07C 7/08
[52] U.S. Cl. ............... 585/864; 203/57; 203/60; 203/63; 203/64; 203/65; 585/833
[58] Field of Search .................... 203/56, 57, 58, 203/60, 62, 63, 64, 65; 585/833, 860, 861, 864, 866

[56] References Cited

U.S. PATENT DOCUMENTS

| | | | |
|---|---|---|---|
| 4,585,526 | 4/1986 | Berg et al. | 203/63 |
| 4,673,465 | 6/1987 | Berg et al. | 203/65 |
| 4,676,875 | 6/1987 | Berg et al. | 203/56 |
| 4,822,947 | 4/1989 | Berg et al. | 203/58 |
| 5,094,723 | 3/1992 | Berg | 203/56 |
| 5,397,441 | 3/1995 | Berg | 203/57 |
| 5,441,608 | 8/1995 | Berg | 203/51 |
| 5,445,715 | 8/1995 | Berg | 203/57 |
| 5,453,167 | 9/1995 | Berg | 585/866 |
| 5,466,345 | 11/1995 | Berg | 203/66 |

*Primary Examiner*—Gary P. Straub

[57] ABSTRACT o-Xylene cannot be separated from p-xylene and m-xylene by conventional distillation or rectification because of the proximity of their boiling points. o-Xylene can be readily separated from mixtures of p-xylene and m-xylene by extractive distillation. Effective agents are o-cresol, dichloroacetic acid, methyl salicylate and 1-tetradecanol.

1 Claim, No Drawings

SEPARATION OF O-XYLENE FROM P-XYLENE AND M-XYLENE BY EXTRACTIVE DISTILLATION

FIELD OF THE INVENTION

This invention relates to a method for separating o-xylene from a mixture with p-xylene and m-xylene using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility an Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 | p-Xylene boils at 138.4° C., m-xylene at 139.1° C. and o-xylene at 144.5° C. The relative volatility of p-xylene from m-xylene is 1.02, for m-xylene from o-xylene it is 1.12 and from p-xylene from o-xylene it is 1.14 and these are virtually impossible to separate by conventional rectification. Extractive distillation would be an attractive method of effecting the separation of o-xylene from p-xylene and m-xylene if agents can be found that (1) will enhance the relative volatility between o-xylene and p-xylene and m-xylene and (2) is easy to recover from the xylenes. The advantage of using extractive distillation in this separation can be seen from the data shown in Table 1. If an agent can be found that will increase the relative volatility to 1.3, 99% purity of m-xylene from o-xylene can be obtained with only 34 plates.

OBJECTIVE OF THE INVENTION

The object of this invention is to provide a process or method of extractive distillation that will enhance the relative volatility of o-xylene from p-xylene and m-xylene in their separation in a rectification column. It is a further object of this invention to identify organic compound extractive distillation agents that are stable and can be separated from xylenes.

SUMMARY OF THE INVENTION

The objects of this invention are provided by a process for the separation of o-xylene from p-xylene and m-xylene which entails the use of certain organic compounds which will enhance the relative volatility of o-xylene from p-xylene and m-xylene when used as the agent in extractive distillation.

DETAILED DESCRIPTION OF THE INVENTION

I have discovered that certain organic compounds will increase the relative volatility of o-xylene from p-xylene and m-xylene when used as the agent in extractive. distillation. The effective agents are o-cresol, dichloroacetic acid, methyl salicylate and 1-tetradecanol.

TABLE 2

Effective Extractive Distillation Agents For Separating o-Xylene From p-Xylene And m-Xylene

| Compound | Relative Volatility |
|---|---|
| None | 1.12 |
| o-Cresol | 1.3 |
| Dichloroacetic Acid | 1.3 |
| Methyl Salicylate | 1.35 |
| 1-Tetradecanol | 1.35 |

WORKING EXAMPLES

Example 1

Fifteen grams of p-xylene, 9 grams of m-xylene and 6 grams of o-xylene and 30 grams of o-cresol were charged to a vapor-liquid equilibrium still and refluxed for 4 hours. Analysis indicated a vapor composition of 53.7% p-xylene, 20.3% m-xylene and 26.0% o-xylene; a liquid composition of 47.8% p-xylene, 19.7% m-xylene and 32.5% o-xylene. This is a relative volatility of m-xylene to o-xylene of 1.3 and of p-xylene to o-xylene of 1.4.

Example 2

Fifteen grams of p-xylene, 9 grams of m-xylene and 6 grams of o-xylene and 30 grams of 1-tetradecanol were charged to a vapor-liquid equilibrium still and refluxed for 7 hours. Analysis indicated a vapor composition of 56.4% p-xylene, 29.6% m-xylene and 14.0% o-xylene; a liquid composition of 51.2% p-xylene, 29.0% m-xylene and 18.8% o-xylene. This is a relative volatility of m-xylene to o-xylene of 1.35 and of p-xylene to o-xylene of 1.45.

I claim:

1. A method for recovering o-xylene from a mixture of o-xylene, p-xylene and m-xylene which comprises distilling a mixture of o-xylene, p-xylene and m-xylene in the presence of an extractive distillation agent, recovering the p-xylene and the m-xylene as overhead product and obtaining the o-xylene and the extractive distillation agent as bottoms product, wherein said extractive distillation agent consists of one material selected from the group consisting of o-cresol, dichloroacetic acid, methyl salicylate and 1-tetradecanol.

* * * * *